(12) United States Patent
Park et al.

(10) Patent No.: US 8,989,095 B2
(45) Date of Patent: Mar. 24, 2015

(54) BAN WIRELESS COMMUNICATION CONTROL METHOD USING SELECTIVE DISCOVERY

(75) Inventors: Kyung Min Park, Daejeon-si (KR); Eun Ji You, Daejeon-si (KR); Hoon Choi, Daejeon-si (KR); Chil Woo Lee, Gwangju-si (KR)

(73) Assignee: Industry Foundation of Chonnan National University, Gwangju-Si (KR)

( * ) Notice: Subject to any disclaimer, the term of this patent is extended or adjusted under 35 U.S.C. 154(b) by 0 days.

(21) Appl. No.: 13/700,189

(22) PCT Filed: Dec. 21, 2011

(86) PCT No.: PCT/KR2011/009961
§ 371 (c)(1),
(2), (4) Date: Nov. 27, 2012

(87) PCT Pub. No.: WO2013/077491
PCT Pub. Date: May 30, 2013

(65) Prior Publication Data
US 2014/0254475 A1     Sep. 11, 2014

(30) Foreign Application Priority Data

Nov. 25, 2011 (KR) .................. 10-2011-0124169

(51) Int. Cl.
*H04W 4/00* (2009.01)
*H04L 12/24* (2006.01)
*H04W 8/00* (2009.01)
*H04W 48/16* (2009.01)

(52) U.S. Cl.
CPC ............... *H04L 41/12* (2013.01); *H04W 8/005* (2013.01); *H04W 48/16* (2013.01)
USPC ............................ 370/328; 709/220; 370/401

(58) Field of Classification Search
None
See application file for complete search history.

(56) References Cited

U.S. PATENT DOCUMENTS

| 2006/0224048 | A1* | 10/2006 | Devaul et al. ................. 600/300 |
| 2008/0164979 | A1* | 7/2008 | Otto ......................... 340/286.01 |
| 2009/0023391 | A1 | 1/2009 | Falck |
| 2009/0270030 | A1* | 10/2009 | Jia et al. .......................... 455/39 |
| 2012/0108267 | A1* | 5/2012 | Yang .......................... 455/456.3 |

FOREIGN PATENT DOCUMENTS

| KR | 1020030088203 A | 11/2003 |
| KR | 1020050027919 A | 3/2005 |
| KR | 1020080090909 A | 10/2008 |
| KR | 1020110050313 A | 5/2011 |
| KR | 1020110069671 A | 6/2011 |

OTHER PUBLICATIONS

Korean Notice of Allowance for application No. 10-2011-0124169 dated Oct. 29, 2013, citing the above reference(s).
International Search Report for application No. PCT/KR2011/009961 dated Nov. 12, 2012, citing the above reference(s).

* cited by examiner

*Primary Examiner* — Bob Phunkulh
(74) *Attorney, Agent, or Firm* — Lowe Hauptman & Ham, LLP

(57) ABSTRACT

The present description relates to a BAN (Body Area Network) wireless communication control method, and more particularly, to a BAN wireless communication control method to which a selective discovery technique is applied. The present invention provides a BAN wireless communication control method, comprising the steps of transmitting a discovery request frame including a selective standard profile, and receiving a discovery response frame from a host that provides at least one of services specified in the selective standard profile.

7 Claims, 7 Drawing Sheets

BAN WIRELESS COMMUNICATION CONTROL METHOD USING SELECTIVE DISCOVERY

TECHNICAL FIELD

The present invention relates to a BAN (Body Area Network) wireless communication control method, and more specifically, to a BAN wireless communication control method using a selective discovery technique.

BACKGROUND ART

An e-textile network is embedded in clothes for small wearable computing devices using a conductive fiber as a communication medium. E-textile networks are integrated for each body using near field communication such as WPAN (Wearable Personal Area Network) since a person can wear a plurality of clothes. In an e-textile network, a host manages a plurality of nodes connected to a conductive fiber and performs wireless communication with other e-textile networks. Accordingly, hosts and nodes existing in different e-textile networks can cooperate with each other to provide services.

An e-textile network can associate or cooperate with other e-textile networks to provide services by discovering neighboring hosts and connecting with a host selected from the discovered hosts.

However, a conventional discovery scheme performs a discovery procedure for all neighboring hosts, and thus resources such as unnecessary discovery of hosts that do not provide a desired service, for example, power and process are wasted.

DETAILED DESCRIPTION OF THE INVENTION

Technical Problems

An object of the present invention is to provide a BAN wireless communication control method capable of preventing waste of discovery host resources by eliminating an unnecessary discovery procedure.

Technical Solutions

According to one aspect of the present invention, a BAN wireless communication control method includes: transmitting a discovery request frame including a selective standard profile; and receiving a discovery response frame from a host that provides at least one of services specified by the selective standard profile.

Advantageous Effects

As described above, the present invention can prevent waste of discovery host resources by performing a discovery procedure only for hosts that provide a service that a coordinator wants to use.

MODE FOR CARRYING OUT THE INVENTION

The above and other aspects of the present invention will be described in detail through preferred embodiments with reference to the accompanying drawings so that the present invention can be easily understood and realized by those skilled in the art. Modifications to the preferred embodiment will be readily apparent to those of ordinary skill in the art, and the disclosure set forth herein may be applied to other embodiments and applications without departing from the spirit and scope of the present invention and the appended claims. In the following description of the present invention, a detailed description of known functions and configurations incorporated herein will be omitted when it may obscure the subject matter of the present invention.

The same reference numbers will be used throughout this specification to refer to the same or like parts.

The present invention can prevent waste of host resource generated during discovery by performing a selective discovery procedure. The selective discovery procedure of the present invention will be described in detail.

First of all, terms used in the following description are defined.

E-textile network: the term 'e-textile network' refers to a body area network that is embedded in clothes using a conductive fiber as a communication medium and used for small wearable computing devices. The e-textile network may mean a network that connects a host to at least one node or a wide area network that connects a plurality of hosts.

Discovery: the term 'discovery' refers to a procedure through which a host of each e-textile network, which functions as a wireless gateway, discovers hosts of other e-textile networks in order to achieve wireless integration of e-textile networks.

Node: the term 'node' refers to a medium that is wirelessly connected to a host and can exchange data or commands with the host. Here, the medium may include a sensor that collects a specific parameter.

Coordinator: the term 'coordinator' refers to a host corresponding to the subject of discovery or a host that starts or initiates a discovery procedure.

Service: the term 'service' refers to all functionalities implemented on a host. Here, the functionalities may include an ability to collect data from a specific sensor.

Selective discovery: the term 'selective discovery' refers to a procedure through which a coordinator discovers only a host that provides at least one of specific services.

Selective standard profile (SSP): the term 'selective standard profile' refers to a selective discovery standard defined in a profile. In other words, 'selective standard profile' means information that specifies a service that a coordinator wants to use through other hosts.

Service profile: the term 'service profile' refers to information that specifies a service provided by each host.

Overview of Discovery Procedure

Figure 1:
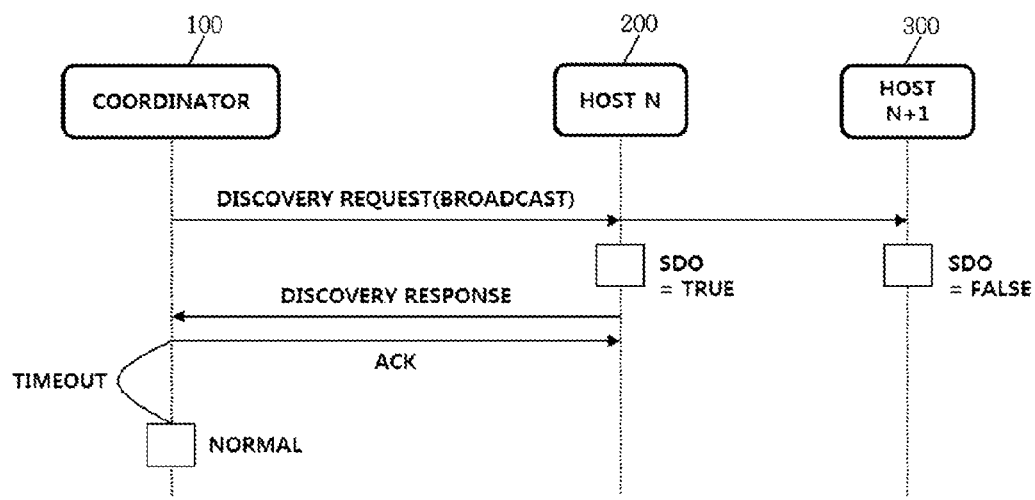
FIG. 1 is a flowchart illustrating a discovery procedure according to a preferred embodiment of the present invention.

A discovery procedure according to a preferred embodiment of the present invention will now be described with reference to FIG. 1. FIG. 1 is a flowchart illustrating a discovery procedure according to a preferred embodiment of the present invention.

In description of the discovery procedure, the term 'coordinator' refers to a subject that initiates the discovery procedure and 'host' refers to a discovery target.

Referring to FIG. 1, a coordinator 100 can broadcast a discovery request frame. The discovery request frame may include a selective standard profile. The selective standard profile may include information that specifies services that the coordinator 100 wants to use. The coordinator 100 can set a timeout such that only a discovery response frame transmitted during a set time is received when broadcasting the discovery request frame. Here, the discovery request frame may be transmitted only to a specific host using previously stored host identification information instead of broadcasting.

Upon receiving the discovery request frame, hosts 200 and 300 can perform a selective discovery operation (SDO). FIG. 1 shows only two hosts for convenience of description. The selective discovery operation may be a process that determines whether the hosts 200 and 300 can provide the services specified by the selective standard profile included in the discovery request frame. Upon performance of the selective discovery operation, the host 200 that can provide at least one of the services that the coordinator 100 wants to use can transmit a discovery response frame to the coordinator 100. The host 300 that cannot provide any of the services that the coordinator 100 wants to use may not transmit a discovery response frame to the coordinator 100. Upon reception of the discovery response frame, the coordinator 100 can discover the host 200 that has transmitted the discovery response frame. The discovery response frame transmitted from the host 200 may include a profile of the host 200, for example, information that specifies the service provided by the host 200 or a host identifier. The coordinator 100 can use the service provided by the host 100 with reference to the profile of the host 200. The present invention does not limit a method by which the coordinator 100 is connected to the discovered host 200 to use the service provided by the host 200. The coordinator 100 may receive all services specified by the selective standard profile from a specific host or receive the services from a plurality of hosts.

Upon reception of the discovery response frame, the coordinator 100 can inform the host 200, which has transmitted the discovery response frame, that the discovery response frame has been successfully received through an ACK frame.

The coordinator 100 can start a timer at the same time when the discovery procedure is performed and end the discovery procedure when a timeout is generated. For example, the timer can be started at the same time when the discovery request frame is broadcast.

The discovery procedure of FIG. 1 is arranged in the following sequence table.

TABLE 1

| Sequence | s | s + 1 | s + 2 | s + 3 | s + 4 |
|---|---|---|---|---|---|
| Coordinator | DRQ | | | ACK | TO |
| Host A | | SDOT | DRS | | |
| Host B | | SDOF | | | |

Figure 2:
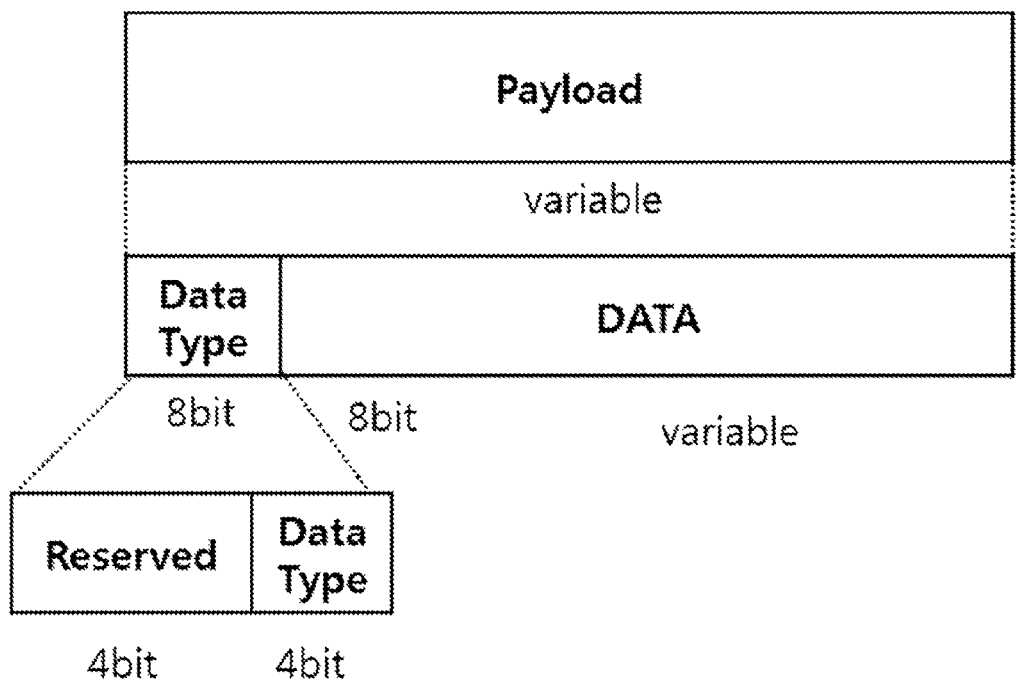
FIG. 2 shows the structure of a payload in a frame used for a discovery procedure according to a preferred embodiment of the present invention.
Figure 3:
FIG. 3 shows the structure of a data type field shown in FIG. 2.

Meaning of abbreviations used in the sequence table is described below.
* DRQ: Discovery Request
* SDOT: Selective Discovery Operation True
* SDOF: Selective Discovery Operation False
* DRS: Discovery Response
* TO: Time Out Basic Structures of Frames Basic structures of frames used for the discovery procedure will now be described with reference to FIGS. 2 and 3. FIG. 2 shows the structure of a payload in a frame used for a discovery procedure according to a preferred embodiment of the present invention. FIG. 3 shows the structure of a data type field shown in FIG. 2.

Referring to FIG. 2, the payload can be divided into a data type field and a data field DATA.

The data type field can represent the property of the frame. Referring to FIG. 3, upper four bits of the data type field can be used as reserved bits and lower four bits can be used to define the property of the frame. Upper two bits of the lower four bits can be used to represent the purpose of a message and the lower two bits thereof can be used to indicate a frame reception state. The upper two bits and the lower two bits can be combined and used. For example, the data type field can be set to '1010' in the case of NACK+discovery response frame. The data type field is represented on a bit-by-bit basis and can have different values according to situation, as shown in Table 2.

TABLE 2

| Bit MSB | | | LSB | Definition | Note |
|---|---|---|---|---|---|
| 0 | 0 | — | — | Frame state | Frame state is checked using lower 2 bits |
| 0 | 1 | — | — | Discovery request | E-textile network is searched |
| 1 | 0 | — | — | Discovery response | Response to discovery |
| — | — | 0 | 0 | ACK | It signals that packet has been successfully received |
| — | — | 0 | 1 | NACK | It signals that packet has not been received. |
| — | — | 1 | 0 | Error | It signals that packet has been abnormally received. |

Referring to FIG. 2, the data field contains data to be actually transmitted and may have a size varying according to data type or communication protocol (e.g. ZigBee or Bluetooth). The data field can be used as a discovery request frame, a discovery response frame and a vacant frame according to data type.

The frame structures shown in FIG. 2 or 3 are maintained and the frame sizes or each field size may be variable.

Discovery Request Frame Structure

Figure 4:
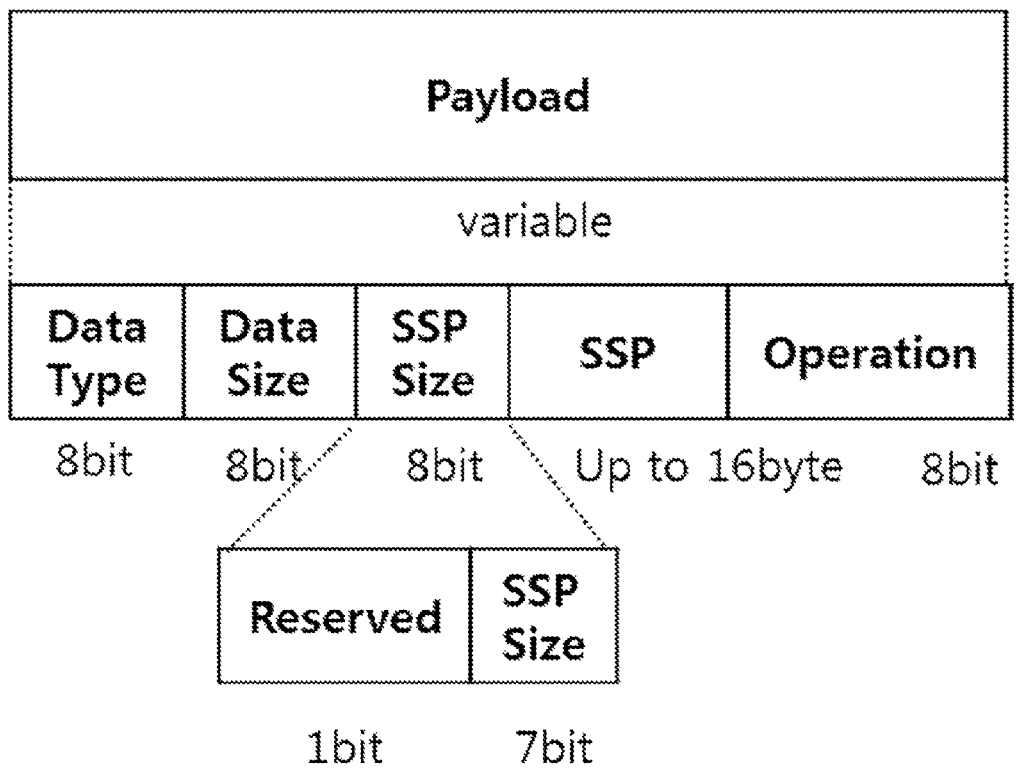
FIG. 4 shows the structure of a discovery request frame according to a preferred embodiment of the present invention.
Figure 5:
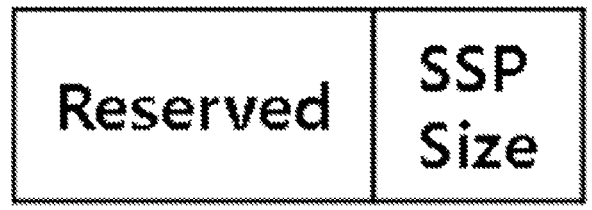
FIG. 5 shows the structure of a selective standard profile size field shown in FIG. 4.

A discovery request frame according to a preferred embodiment of the present invention will now be described with reference to FIGS. 4 and 5. FIG. 4 shows the structure of a discovery request frame according to a preferred embodiment of the present invention. FIG. 5 shows the structure of a selective standard profile size field shown in FIG. 4.

Referring to FIG. 4, the payload in the discovery request frame can include a data type field (Data Type), a data size field (Data Size), a selective standard profile size field (SSP Size), a selective standard profile field (SSP) and an operator field (Operation).

The data type field is as descried above.

The data size field represents the payload size, for example, the number of bytes of the payload and can have a value of 0 to 18. When the selective standard profile size is 0, the data size field is considered to include no data, and thus the data size field can have a value of 0.

The selective standard profile size field represents the selective standard profile field size, for example, the number of bits of the selective standard profile and can have a value of 0 to 128. Referring to FIG. 5, only 7 bits of the selective standard profile size field except 1-bit reserved field can be used to represent the selective standard profile size.

Referring back to FIG. 4, the selective standard profile field can define a selective discovery standard. A service that the coordinator wants to use can be specified using at least one bit allocated to the selective standard profile field. Preferably, 1 bit can be used to specific one service. Accordingly, it is possible to minimize consumption of resources of a coordinator or a host during selective discovery, for example, operations, packet processing and power consumption in a selective discovery operation. Furthermore, it is possible to maximize the number of service types that can be defined by selective discovery. If 16 bytes are allocated to the selective standard profile field and 1 bit is allocated to specify one service, up to 128 (16*8) selective discovery standards can be defined. Different service types can be assigned to bit positions in the selective standard profile. That is, each bit in the selective standard profile can be allocated to a specific service type. Specifically, to use a specific service (service A), a bit value allocated to the service A in the selective standard profile can be set to '1'. Otherwise, when a specific service (service B) is not used, a bit value allocated to the service B in the selective standard profile can be set to '0'. Provided that four bits are allocated to the selective standard profile and the most significant bit (MSB) to the least significant bit (LSB) are sequentially assigned to a body heat sensing service, an external temperature sensing service, an electrocardiogram sensing service and a pulse sensing service, the selective standard profile can be set to '1100' when a coordinator wants to discover a host that provides at least one of the body heat sensing service and the external temperature sensing service through selective discovery. In the following description, if a bit value is set to '1' in the selective standard profile, a service to which the bit set to '1' is allocated is considered to be specified. As described below, a host can match the selective standard profile with the service profile thereof or perform an operation on the selective standard profile and the service profile upon receiving the selective standard profile. When it is determined that that the host provides at least one service or all services specified by the selective standard profile from the matching or operation result, the host can transmit a discovery response frame to the coordinator.

The operator field may represent an operator used for the host that has received the discovery request frame to perform an operation on the service profile of the host and the selective standard profile. For example, the operator can be represented by an ASCII code having a value of '&' or '|'.

The frame structures shown in FIGS. 4 and 5 are maintained and the frame sizes or each field size may be variable. Otherwise, some fields may be omitted.

Discovery Response Frame Structure

Figure 6:
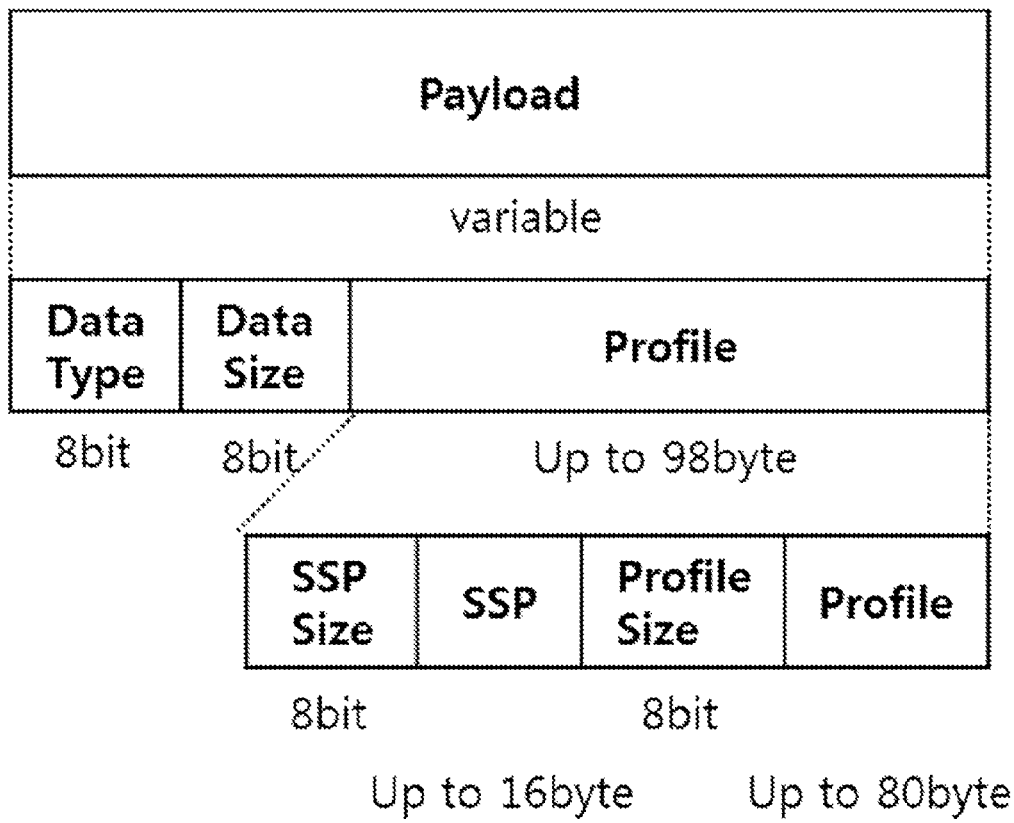
FIG. 6 shows the structure of a discovery response frame according to a preferred embodiment of the present invention.

A discovery response frame according to a preferred embodiment of the present invention will now be described with reference to FIG. 6. FIG. 6 shows the structure of a discovery response frame according to a preferred embodiment of the present invention.

Referring to FIG. 6, a payload in the discovery response frame may include a data type field (Data Type), a data size field (Data Size), and a profile field (Profile). Here, the profile field may include a selective standard profile size field (SSP Size), a selective standard profile field (SSP), a profile size field (Profile Size), and a profile (Profile).

The data type field (Data Type), the data size field (Data Size), the selective standard profile size field (SSP Size) and the selective standard profile field (SSP) correspond to those in the above-described discovery request frame.

The profile size field represents the profile size, for example, the number of bytes of the profile and may have a value in the range of 0 to 80.

The profile may be information that can represent characteristics of the corresponding e-textile network in addition to the selective standard profile. The profile may be variable according to communication protocol. For example, the profile may include a host identifier or a host service profile. The service profile can specify a service provided by a host. The service profile can specify the service provided by the host in the same format as that of the above-mentioned selective standard profile. That is, the same bit position in the selective standard profile and the service profile can be allocated to the same service and the sizes of the selective standard profile and the service profile, that is, the numbers of bits allocated to the selective standard profile and the service profile can be equal to each other.

Selective Discovery Operation (SDO)

A selective discover operation is a process of determining whether a host that has received a discovery request frame provides at least one service or all services specified by the selective standard profile.

To perform the selective discovery operation, a host can use an operator ('&' or '|') defined by the operator field of the discovery request frame. A case in which '&' is used is described in detail. In this case, it is assumed that a service is specified by one bit.

The host sequentially performs an AND operation on bit values in the selective standard profile and bit values in the service profile on a bit-by-bit basis according to orders of the bit values, for example, from the MSB to the LSB. The operation result is shown in Table 3.

TABLE 3

| Operation symbol | Definition | | Operation result |
|---|---|---|---|
| '&' | Host provides all services on SSP | TRUE | Host service profile (bit operation &) Frame SSP == host SSP |
| | | FLASE | Host service profile (bit operation &) Frame SSP != host SSP |
| | Host provides only some service on SSP | TRUE | Host service profile (bit operation &) Frame SSP > 0 |
| | | FALSE | Host service profile (bit operation &) Frame SSP == 0 |

In Table 3, 'Host service profile (bit operation &) frame SSP==host SSP' means that the host provides all services that the coordinator wants to use.

'Host service profile (bit operation &) frame SSP!=host SSP' means that the host provides part of the services that the coordinator wants to use.

'Host service profile (bit operation &) frame SSP>0' means that the host provides part of the services that the coordinator wants to use. In this case, a result of an '&' operation performed on bit values in the same position in the selective standard profile and the service profile may include at least one value '1'.

'Host service profile (bit operation &) frame SSP==0' means that the host provides no service that the coordinator wants to use.

A host for which the operation result is determined as 'TRUE' can transmit a discovery response frame to the coordinator. Whether the host transmits the discovery response frame to the coordinator in the case of 'Host service profile (bit operation &) frame SSP==host SSP' or in the case of 'Host service profile (bit operation &) frame SSP>0' can be determined by a designer. It is also possible to set the host such that the host transmits the discovery response frame to the coordinator in both cases of 'Host service profile (bit operation &) frame SSP==host SSP' and 'Host service profile (bit operation &) frame SSP>0'.

The selective discovery operation will now be described in detail. It is assumed that the selective standard profile and the service profile are set as shown in Table 4, bits in the same position in the selective standard profile and the service profile are allocated to the same service, and the sizes of the selective standard profile and the service profile, that is, the numbers of bits allocated to the selective standard profile and the service profile are equal to each other. In addition, it is assumed that the selective standard profile and the service profile have a size of 4 bits, and the MSB to LSB are sequentially assigned to a body heat sensing service, an external temperature sensing service, an electrocardiogram sensing service and a pulse sensing service. Furthermore, it is assumed that the operator field is set to '&' in the discovery request frame.

TABLE 4

| Selective standard profile | Host service profile | | |
| --- | --- | --- | --- |
| | Host A | Host B | Host C |
| 1100 (selective standard profile generated by the coordinator to selectively discover a host that provides the body heat sensing service and/or external temperature sensing service) | 1000 (host A provides only the body heat sensing service) | 1100 (host B provides the body heat sensing service and external temperature service) | 0011 (host C does not provide any of the body heat sensing service and external temperature sensing service) |
| Selective discovery operation result | 1000 | 1100 | 0000 |

In this case, an operation result with respect to host A may be 'host service profile (bit operation &) frame SSP!=host SSP' or 'host service profile (bit operation &) frame SSP>0'. An operation result with respect to host B may be 'host service profile (bit operation &) frame SSP==host SSP'. An operation result with respect to host C may be 'host service profile (bit operation &) frame SSP==0'.

In this case, host A and/or host B can transmit a discovery response frame to the coordinator according to setting.

As described above, it is possible to achieve optimized selective discovery by allocating one bit to each service in the selective standard profile and the service profile and implementing the selective discovery operation using only operation '&'. This selective discovery scheme can perform discovery with minimum resource (power, computing, etc.)

Those skilled in the art can change frame structures and sizes, arrangement and sizes of fields in a frame, the number of bits allocated to each service in the selective standard profile and the service profile, and an operation technique used to implement the selective discovery operation, according to a designer's intention.

Methods for processing frame loss and error that may be generated during a discovery procedure will now be described with reference to FIGS. 7 to 11.

Case in which Discovery Response Frame is Lost During Discovery Procedure

Figure 7:
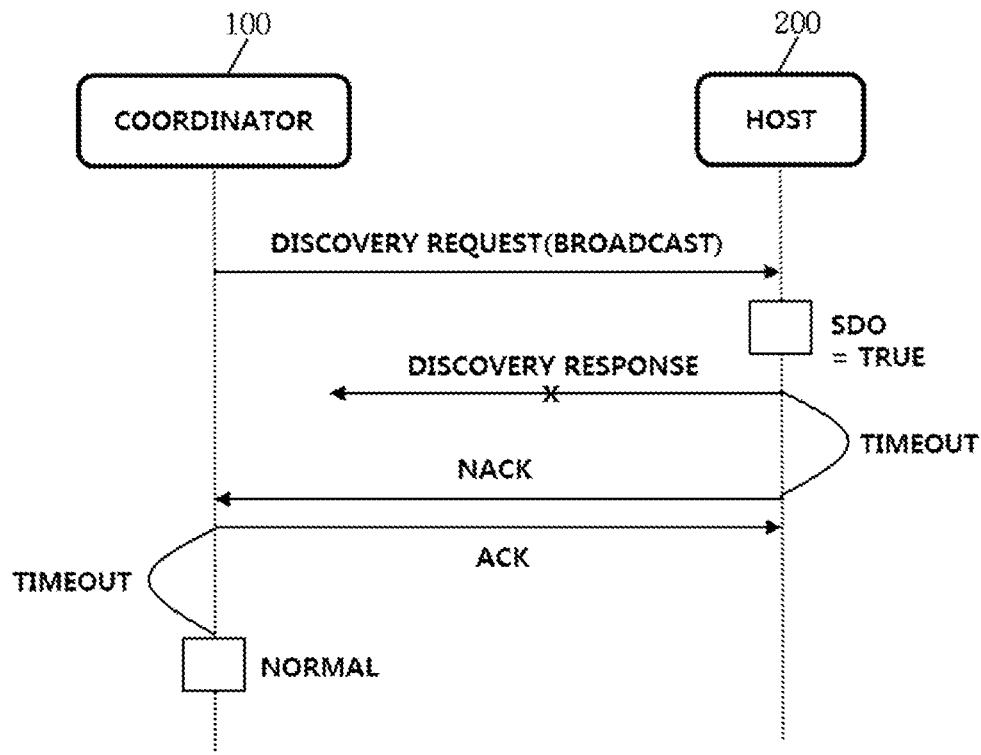
FIG. 7 is a flowchart illustrating a processing method when a discovery response frame is lost.

A processing method when a discovery response frame is lost during a discovery procedure will now be described with reference to FIG. 7. FIG. 7 is a flowchart illustrating a processing method when a discovery response frame is lost.

FIG. 7 shows a case in which a host receives a discovery request frame and transmits a discovery response frame to a coordinator because a selective discovery operation result is 'TRUE', but the discovery response frame is lost. In this case, when the host does not receive an ACK frame for a predetermined period of time from when the discovery request frame is transmitted, the host can transmit a NACK+discovery response frame. Here, the data type field may be set to '1010' as described above.

The process of FIG. 7 is arranged in the following sequence table.

TABLE 5

| | Sequence | | | | | | |
| --- | --- | --- | --- | --- | --- | --- | --- |
| | S | s + 1 | s + 2 | s + 3 | s + 4 | s + 5 | s + 6 |
| Coordinator | DRQ | | | | | ACK | TI |
| Host A | | SDOT | DRS(x) | TI | NACK + DRS | | |

Case in which ACK Frame is Lost During Discovery Procedure

Figure 8:
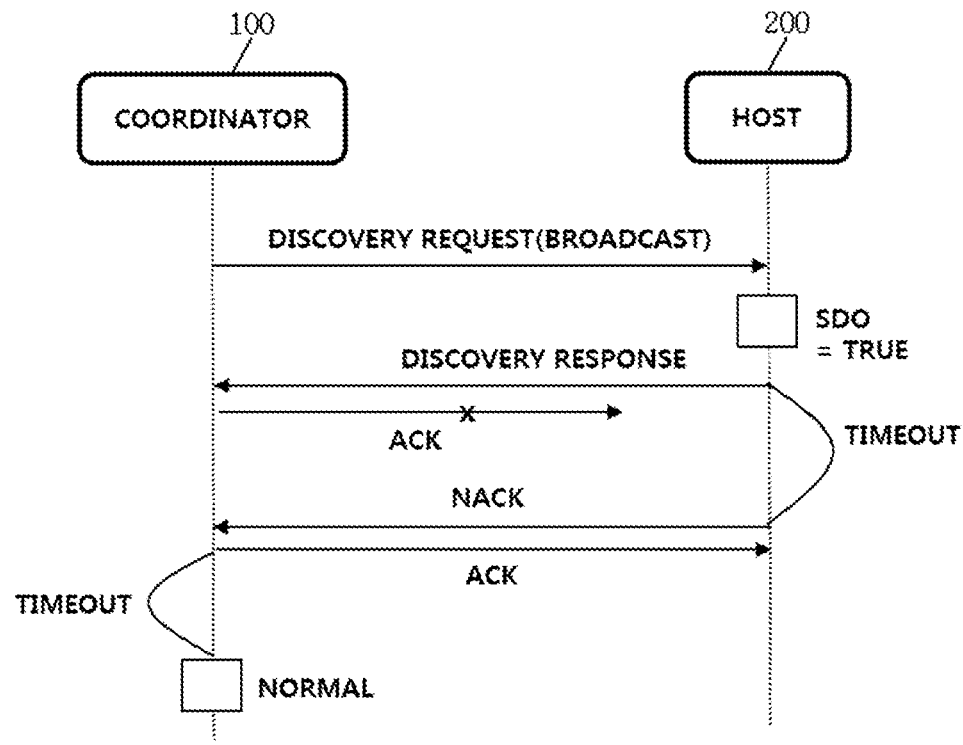
FIG. 8 is a flowchart illustrating a processing method when an ACK frame is lost.

A processing method when an ACK frame is lost during a discovery procedure will now be described with reference to FIG. 8. FIG. 8 is a flowchart illustrating a processing method when an ACK frame is lost.

FIG. 8 shows a case in which an ACK frame is lost although the coordinator transmits the ACK frame in response to a discovery response frame. In this case, when the host does not receive an ACK frame for a predetermined period of time from when the discovery response frame is transmitted, the host can retransmit a NACK+discovery response frame.

The process of FIG. 8 is arranged in the following sequence table.

TABLE 6

| | Sequence | | | | | | | |
| --- | --- | --- | --- | --- | --- | --- | --- | --- |
| | s | s + 1 | s + 2 | s + 3 | s + 3 | s + 4 | s + 5 | s + 6 |
| Coordinator | DRQ | | | ACK(x) | | | ACK | TI |
| Host A | | SDOT | DRS | | TI | NACK + DRS | | |

Figure 9:
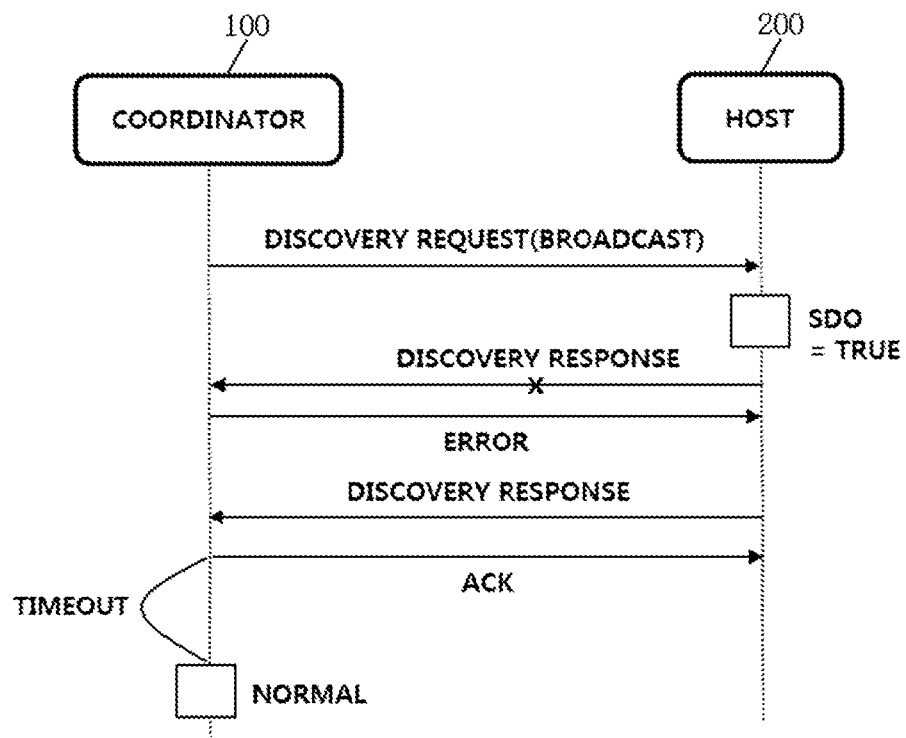
FIG. 9 is a flowchart illustrating a processing method when an error is generated in a discovery response frame during a discovery procedure.

Case in which Error is Generated in Discovery Response Frame During Discovery Procedure A processing method when an error is generated in a discovery response frame during a discovery procedure will now be described with reference to FIG. 9. FIG. 9 is a flowchart illustrating a processing method when an error is generated in a discovery response frame during a discovery procedure.

FIG. 9 shows a case in which an error is generated in the discovery response frame transmitted from the host. In this case, when the coordinator detects the error from the discovery response frame, the coordinator can transmit an error frame. Upon reception of the error frame, the host can transmit an ERROR+discovery response frame.

The process of FIG. 9 is arranged in the following sequence table.

TABLE 7

| | Sequence | | | | | |
|---|---|---|---|---|---|---|
| | s | s + 1 | s + 2 | s + 3 | s + 4 | s + 5 | s + 6 |
| Coordinator | DRQ | | | ERROR | | ACK | TI |
| Host A | | SDOT | DRS(E) | | ERROR + DRS | | |

Case in which Error is Generated in ACK Frame During Discovery Procedure

Figure 10:
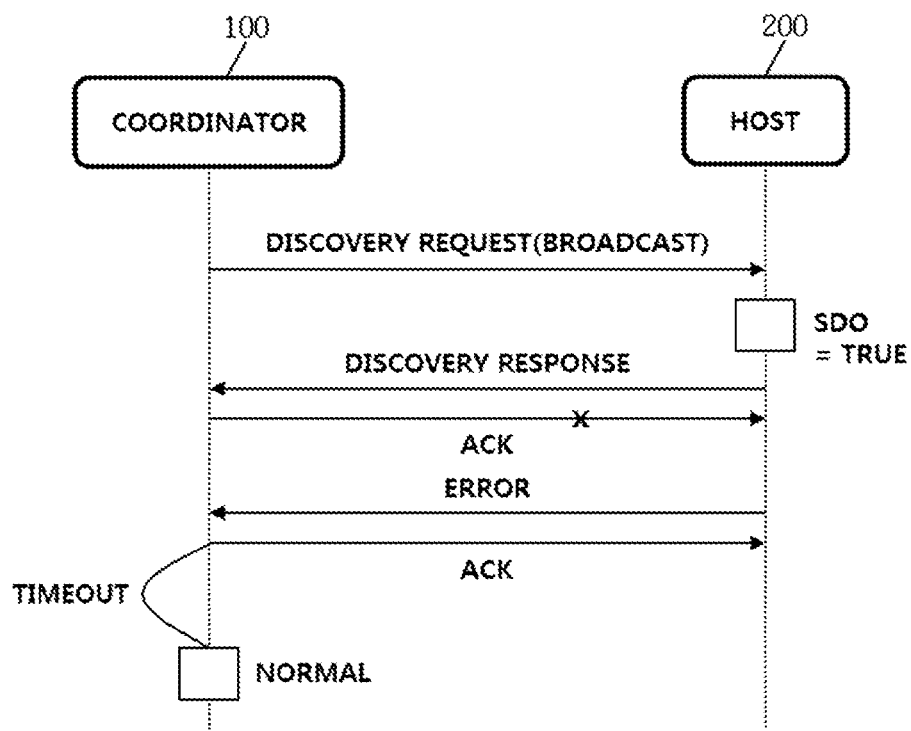
FIG. 10 is a flowchart illustrating a processing method when an error is generated in an ACK frame during a discovery procedure.

A processing method when an error is generated in an ACK frame during a discovery procedure will now be described with reference to FIG. 10. FIG. 10 is a flowchart illustrating a processing method when an error is generated in an ACK frame during a discovery procedure.

FIG. 10 shows a case in which an error is generated in the ACK frame transmitted from the coordinator. When the host detects the error from the ACK frame, the host can transmit an error frame. Upon reception of the error frame, the coordinator can retransmit an ACK frame.

The process of FIG. 10 is arranged in the following sequence table.

TABLE 8

| | Sequence | | | | | |
|---|---|---|---|---|---|---|
| | s | s + 1 | s + 2 | s + 3 | s + 4 | s + 5 | s + 6 |
| Coordinator | DRQ | | | ACK(E) | | ACK | TI |
| Host A | | SDOT | DRS | | ERROR | | |

Case in which Two or More Retransmissions Occur During Discovery Procedure

Figure 11:
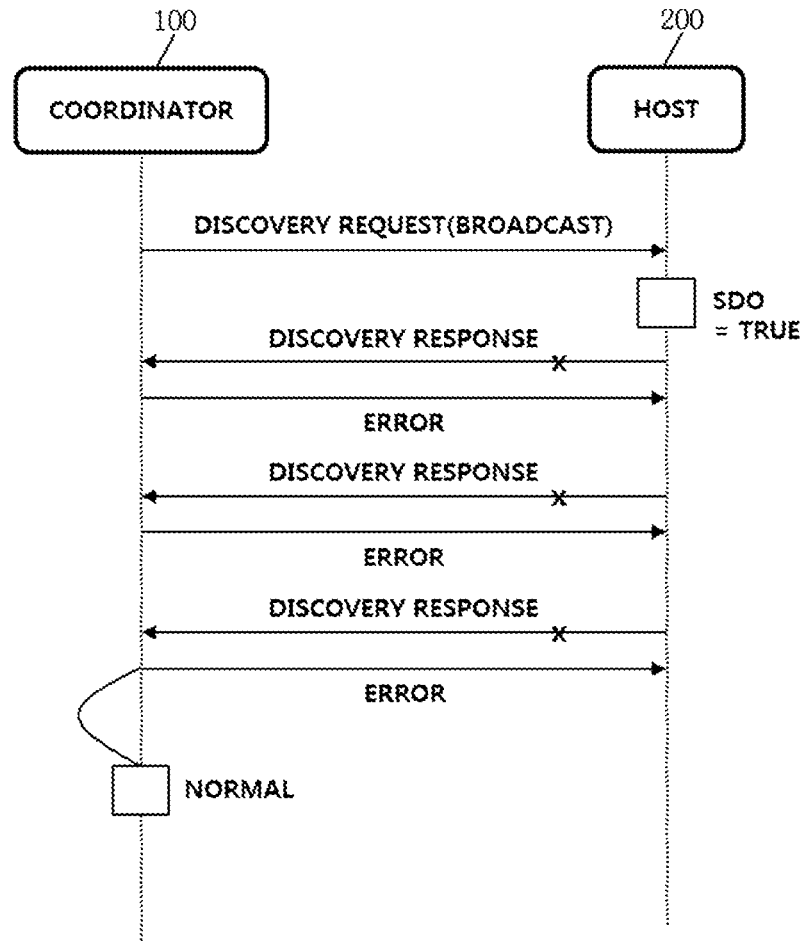
FIG. 11 is a flowchart illustrating a processing method when two or more retransmissions occur during a discovery procedure.

A processing method when two or more retransmissions occur during a discovery procedure will now be described with reference to FIG. 11. FIG. 11 is a flowchart illustrating a processing method when two or more retransmissions occur during a discovery procedure.

When a timeout is generated in the host or the host or the coordinator receives a frame having an error, a discovery response frame can be retransmitted. However, when the number of retransmissions exceeds two, the host can stop the procedure and return to the initial state.

The process of FIG. 11 is arranged in the following sequence table.

TABLE 9

| Sequence | s | s + 1 | s + 2 | s + 3 | s + 3 |
|---|---|---|---|---|---|
| Coordinator Host A | DRQ | SDOT | DRS(E) | ERROR | ERROR + DRS(E) |
| Sequence Coordinator Host A | s + 4 ERROR | s + 5 ERROR + DRS(E) | s + 6 ERROR | s + 8 TI | |

State changes in a coordinator and a host according to a preferred embodiment of the present invention will be described with reference to FIGS. 12 and 13. Explanation of parts corresponding to the above-described is omitted or simplified.

State Change in Coordinator

Figure 12:
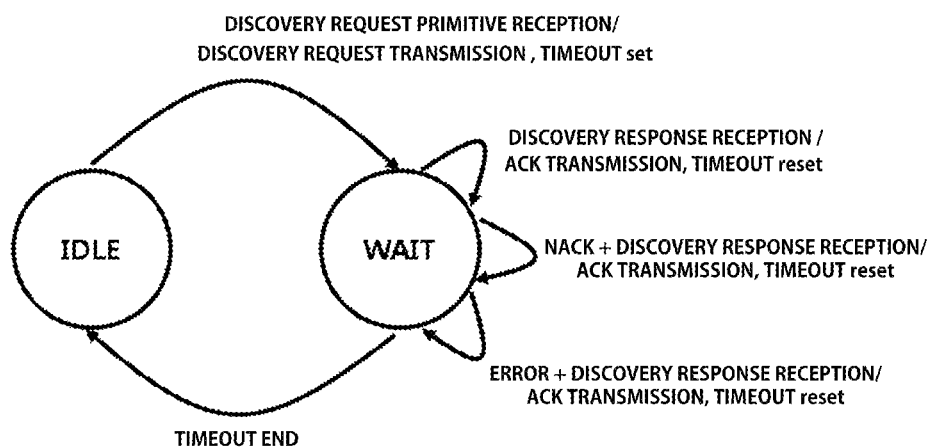
FIG. 12 illustrates state change in a coordinator during a discovery procedure.

FIG. 12 illustrates state change in a coordinator during a discovery procedure.

Referring to FIG. 12, the coordinator may have idle and wait states.

(A) IDLE State

When the coordinator starts to operate, the coordinator waits for an internal event in an idle state. The internal event may be a process through which an application processor operating in the coordinator calls a link layer protocol primitive. In the idle state, state transition may occur when a discovery request primitive is received. Upon reception of the discovery request primitive, the coordinator broadcasts a discovery request frame. When transmission of the discovery request frame is ended, the coordinator can set and start a timeout and change to a wait state.

(B) WAIT State

In the wait state, three events (discovery response frame reception/NACK+discovery response frame reception/ERROR+discovery response frame reception) and one transition (completion of timeout) may be generated.

1. Generation of discovery response frame reception event: the coordinator can successfully receive a discovery response frame in response to the discovery request frame from a host. The coordinator can transmit an ACK frame and re-set a timeout.

2. Reception of NACK+discovery response frame: the coordinator can receive NACK+discovery response frame when the host does not receive the ACK frame. The coordinator can transmit an ACK frame and re-set a timeout.

3. Reception of ERROR+discovery response frame: the coordinator can receive ERROR+discovery response frame when an error is generated in a frame transmitted from the host. The coordinator can transmit an ACK frame and re-set a timeout.

4. Completion of timeout: when the timeout starts and a threshold time ends without generation of an event, the coordinator can determine that discovery is ended and change to the idle state.

State Change in Host

Figure 13:
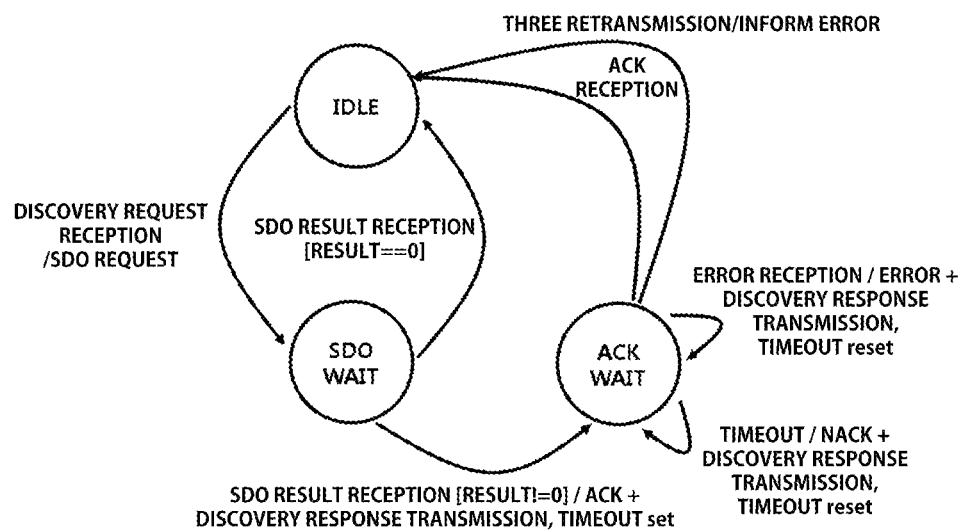
FIG. 13 illustrates state change in a host during a discovery procedure.

FIG. 13 illustrates state change in a host during a discovery procedure.

Referring to FIG. 13, a host may have an idle SDO wait state and an ACK wait state.

(A) IDLE State

When the host starts to operate, the host can wait for an internal state in the idle state. When the host receives a discovery response frame in the idle state, state transition may occur. Upon reception of the discovery response frame, the host can request a selective discovery operation to a higher layer and change to an SDO wait state.

(B) SDO Wait State

In the SDO wait state, the host can perform state transition according to a result of SDO, received from the higher layer. When the SDO result is '0', the host can change to the idle state without performing any operation. The host can transmit a discovery response frame when the SDO result is not '0'. After transmission of the frame, the host can set and start a timeout and change to an ACK wait state.

(C) ACK Wait State

In the ACK wait state, two events and two transitions (ERROR frame reception/timeout end/ACK frame reception/three retransmissions) may occur.

1. ERROR frame reception: the host can transmit ERROR+ discovery response frame upon receiving an ERROR frame from the coordinator. After transmission of the frame, the host can re-set the timeout.

2. Completion of timeout: when the host does not receive an ACK frame after the timeout starts and a critical time is ended, the host can transmit NACK+discovery response frame.

3. ACK frame reception: upon reception of an ACK frame from the coordinator, the host determines that communication has been successfully finished and can change to an idle state.

4. Three retransmissions: when the number of retransmissions reaches three because the timeout is ended or an error is generated in a frame, the host determines that discovery has been abnormally ended and can change to the idle state.

The BAN wireless communication control method according to the embodiments of present invention may be implemented as program commands that can be executed by various computer means and written to a computer-readable recording medium. The computer-readable recording medium may include a program command, a data file, a data structure, etc. alone or in combination. The program commands written to the medium are designed or configured especially for the present invention, or known to those skilled in computer software. Examples of the computer-readable recording medium include magnetic media such as a hard disk, a floppy disk, and a magnetic tape, optical media such as a CD-ROM and a DVD, magneto-optical media such as a floptical disk, and a hardware device configured especially to store and execute a program command, such as a ROM, a RAM, and a flash memory.

The processor-readable recording medium can be distributed over a plurality of computer systems connected to a network so that processor-readable code is written thereto and executed therefrom in a decentralized manner. Programs, code, and code segments to realize the embodiments herein can be construed by one of ordinary skill in the art.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for controlling BAN wireless communication, the method comprising:
    transmitting a discovery request frame including a selective standard profile by a coordinator; and
    receiving a discovery response frame including a service profile from a host that provides at least one of services specified by the selective standard profile,
    wherein the selective standard profile specifies at least one service requested by the coordinator,
    wherein the service profile specifies a service provided by the host in the same format as the selective standard profile, and
    wherein the selective standard profile and the service profile allocate one bit per service.

2. The method of claim 1,
    wherein the host performs an operation on the selective standard profile and the service profile to determine whether the host provides at least one of the services specified by the selective standard profile,
    wherein, when it is determined that the host provides at least one of the services specified by the selective standard profile, the host generates the discovery response frame.

3. The method of claim 2, wherein bits in the same position in the service profile and the selective standard profile are allocated to the same service, and the host determines whether the host provides at least one of the services specified by the selective standard profile by performing an AND operation on bits in the same bit order in the service profile and the selective standard profile.

4. The method of claim 2, wherein the discovery request frame includes operator information used for the host to perform an operation on the selective standard profile and the service profile.

5. A non-transitory computer readable recording medium storing a program for executing:
    transmitting a discovery request frame including a selective standard profile by a coordinator; and
    receiving a discovery response frame including a service profile from a host that provides at least one of services specified in the selective standard profile,
    wherein the selective standard profile specifies at least one service requested by the coordinator,
    wherein the service profile specifies a service provided by the host in the same format as the selective standard profile, and
    wherein the selective standard profile and the service profile allocate one bit per service.

6. A BAN wireless communication control method, comprising:
    transmitting a discovery request frame including a selective standard profile; and
    receiving a discovery response frame from a host that provides at least one of services specified by the selective standard profile,
    wherein the host performs an operation on the selective standard profile and a service profile to determine whether the host provides the services specified by the selective standard profile, the service profile being information that specifies a service provided by the host,
    wherein, when it is determined that the host provides at least one of the services specified by the selective standard profile, the host generates the discovery response frame,
    wherein the service profile specifies the service provided by the host in the same format as the selective standard profile, and
    wherein bits in the same position in the service profile and the selective standard profile are allocated to the same service, and the host determines whether the host provides the services specified by the selective standard profile by performing an AND operation on bits in the same bit order in the service profile and the selective standard profile.

7. The BAN wireless communication control method according to claim 6, wherein the service profile and the selective standard profile allocate one bit per service.

* * * * *